US011026696B2

(12) United States Patent
Zammataro

(10) Patent No.: US 11,026,696 B2
(45) Date of Patent: *Jun. 8, 2021

(54) ENDOSCOPIC CLIP APPLIER

(71) Applicant: Covidien LP, Mansfield, MA (US)

(72) Inventor: Thomas Zammataro, Hamden, CT (US)

(73) Assignee: COVIDIEN LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/174,967

(22) Filed: Oct. 30, 2018

(65) Prior Publication Data

US 2019/0059904 A1 Feb. 28, 2019

Related U.S. Application Data

(63) Continuation of application No. 15/356,741, filed on Nov. 21, 2016, now Pat. No. 10,159,492, which is a continuation of application No. 13/865,412, filed on Apr. 18, 2013, now Pat. No. 9,532,787.

(60) Provisional application No. 61/653,593, filed on May 31, 2012.

(51) Int. Cl.
*A61B 17/128* (2006.01)
*A61B 17/10* (2006.01)

(52) U.S. Cl.
CPC .......... *A61B 17/1285* (2013.01); *A61B 17/10* (2013.01)

(58) Field of Classification Search
CPC .... A61B 17/1285; A61B 17/10; A61B 17/068
See application file for complete search history.

(56) References Cited

U.S. PATENT DOCUMENTS

| 3,120,230 A | 2/1964 | Skold |
| 3,363,628 A | 1/1968 | Wood |
| 3,638,847 A | 2/1972 | Noiles et al. |

(Continued)

FOREIGN PATENT DOCUMENTS

| AU | 2010200641 A1 | 10/2010 |
| AU | 2013254887 A1 | 11/2013 |

(Continued)

OTHER PUBLICATIONS

Extended European Search Report corresponding to EP 13 16 6382.5, completed Nov. 19, 2013 and dated Nov. 28, 2013; (8 pp).

(Continued)

*Primary Examiner* — Katherine M Rodjom

(57) ABSTRACT

An endoscopic surgical clip applier is provided, wherein a distal end of the surgical clip applier is introduced to a target surgical site through a cannula having a fixed diameter lumen. The surgical clip applier comprises an endoscopic portion supported by and extending from a handle assembly, and a pair of jaws supported at a distal end of an outer tube, wherein the pair of jaws are movable between a fully open condition and approximated conditions. When the pair of jaws are in the fully open condition the pair of jaws extend radially beyond an outer diameter of the outer tube to a dimension greater than the fixed diameter of the lumen of the cannula; and when the pair of jaws are in at least one approximated condition the pair of jaws have a transverse dimension permitting passage through the lumen of the cannula.

20 Claims, 9 Drawing Sheets

(56) References Cited

U.S. PATENT DOCUMENTS

| | | |
|---|---|---|
| 3,675,688 A | 7/1972 | Bryan et al. |
| 3,735,762 A | 5/1973 | Bryan et al. |
| 3,867,944 A | 2/1975 | Samuels |
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |

(56) References Cited

U.S. PATENT DOCUMENTS

| | | |
|---|---|---|
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |

(56) References Cited

U.S. PATENT DOCUMENTS

| | | |
|---|---|---|
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B2 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |

(56) References Cited

U.S. PATENT DOCUMENTS

| | | |
|---|---|---|
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,885 B2 | 5/2011 | Sixto, Jr. et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,048,088 B2 | 11/2011 | Green et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,609,109 B2 | 12/2013 | Donnelly et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |

(56) References Cited

U.S. PATENT DOCUMENTS

| | | |
|---|---|---|
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,828,023 B2 | 9/2014 | Neff et al. |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,920,438 B2 | 12/2014 | Aranyi et al. |
| 8,939,974 B2 | 1/2015 | Boudreaux et al. |
| 8,945,151 B2 | 2/2015 | Salas |
| 8,950,646 B2 | 2/2015 | Viola |
| 8,961,542 B2 | 2/2015 | Whitfield et al. |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,972 B1 | 3/2016 | Patel et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,810 B2 | 9/2016 | Cappola |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,526,565 B2 | 12/2016 | Strobl |
| 9,532,787 B2 * | 1/2017 | Zammataro ............ A61B 17/10 |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 * | 12/2018 | Zammataro ............ A61B 17/10 |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2001/0047178 A1 | 11/2001 | Peters |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0123742 A1 | 9/2002 | Baxter et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto et al. |
| 2002/0198540 A1 | 12/2002 | Smith et al. |
| 2002/0198541 A1 | 12/2002 | Smith et al. |
| 2003/0014060 A1 | 1/2003 | Wilson et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake |
| 2003/0167063 A1 | 9/2003 | Kerr |
| 2003/0208231 A1 | 11/2003 | Williamson et al. |
| 2003/0220657 A1 | 11/2003 | Adams |
| 2003/0225423 A1 | 12/2003 | Huitema |
| 2003/0229360 A1 | 12/2003 | Gayton |
| 2003/0233105 A1 | 12/2003 | Gayton |
| 2004/0010272 A1 | 1/2004 | Manetakis et al. |
| 2004/0044352 A1 | 3/2004 | Fowler et al. |
| 2004/0097970 A1 | 5/2004 | Hughett |
| 2004/0097971 A1 | 5/2004 | Hughett |
| 2004/0097972 A1 | 5/2004 | Shipp et al. |
| 2004/0106936 A1 | 6/2004 | Shipp et al. |
| 2004/0133215 A1 | 7/2004 | Baxter |
| 2004/0138681 A1 | 7/2004 | Pier |
| 2004/0153100 A1 | 8/2004 | Ahlberg et al. |

(56) References Cited

U.S. PATENT DOCUMENTS

| | | |
|---|---|---|
| 2004/0158266 A1 | 8/2004 | Damarati |
| 2004/0162567 A9 | 8/2004 | Adams |
| 2004/0167545 A1 | 8/2004 | Sadler et al. |
| 2004/0176776 A1 | 9/2004 | Zubok et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0080440 A1 | 4/2005 | Durgin et al. |
| 2005/0085830 A1 | 4/2005 | Lehman et al. |
| 2005/0090837 A1 | 4/2005 | Sixto et al. |
| 2005/0090838 A1 | 4/2005 | Sixto et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0000867 A1 | 1/2006 | Shelton et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi et al. |
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0111731 A1 | 5/2006 | Manzo |
| 2006/0124485 A1 | 6/2006 | Kennedy |
| 2006/0129170 A1 | 6/2006 | Royce et al. |
| 2006/0135992 A1 | 6/2006 | Bettuchi et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0212050 A1 | 9/2006 | D'Agostino et al. |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0241655 A1 | 10/2006 | Viola |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0021766 A1 | 1/2007 | Belagali et al. |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | de la Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0066981 A1 | 3/2007 | Meagher |
| 2007/0073314 A1 | 3/2007 | Gadberry et al. |
| 2007/0083218 A1 | 4/2007 | Morris |
| 2007/0093790 A1 | 4/2007 | Downey et al. |
| 2007/0093856 A1 | 4/2007 | Whitfield et al. |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203509 A1 | 8/2007 | Bettuchi |
| 2007/0203510 A1 | 8/2007 | Bettuchi |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |

(56) References Cited

U.S. PATENT DOCUMENTS

| | | |
|---|---|---|
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0065119 A1 | 3/2008 | Viola |
| 2008/0103510 A1 | 5/2008 | Taylor et al. |
| 2008/0140090 A1 | 6/2008 | Aranyi et al. |
| 2008/0147092 A1 | 6/2008 | Rogge et al. |
| 2008/0147093 A1 | 6/2008 | Roskopf et al. |
| 2008/0154287 A1 | 6/2008 | Rosenberg et al. |
| 2008/0167665 A1 | 7/2008 | Arp et al. |
| 2008/0228199 A1 | 9/2008 | Cropper et al. |
| 2008/0243145 A1 | 10/2008 | Whitfield et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312665 A1 | 12/2008 | Shibata et al. |
| 2008/0312670 A1 | 12/2008 | Lutze et al. |
| 2008/0319456 A1 | 12/2008 | Hart |
| 2009/0076533 A1 | 3/2009 | Kayan et al. |
| 2009/0088777 A1 | 4/2009 | Miyagi et al. |
| 2009/0088783 A1 | 4/2009 | Kennedy et al. |
| 2009/0171380 A1 | 7/2009 | Whiting |
| 2009/0182193 A1 | 7/2009 | Whitman et al. |
| 2009/0204115 A1 | 8/2009 | Dees, Jr. et al. |
| 2009/0209946 A1 | 8/2009 | Swayze et al. |
| 2009/0222003 A1 | 9/2009 | Otley |
| 2009/0228023 A1 | 9/2009 | Cui |
| 2009/0228024 A1 | 9/2009 | Whitfield et al. |
| 2009/0261142 A1 | 10/2009 | Milliman et al. |
| 2009/0264904 A1 | 10/2009 | Aldrich et al. |
| 2009/0299382 A1 | 12/2009 | Zergiebel |
| 2009/0312775 A1 | 12/2009 | Gilkey et al. |
| 2009/0326558 A1 | 12/2009 | Cui et al. |
| 2010/0049216 A1 | 2/2010 | Zergiebel |
| 2010/0057102 A1 | 3/2010 | Sorrentino et al. |
| 2010/0057103 A1 | 3/2010 | Sorrentino et al. |
| 2010/0057104 A1 | 3/2010 | Sorrentino et al. |
| 2010/0057105 A1 | 3/2010 | Sorrentino et al. |
| 2010/0057106 A1 | 3/2010 | Sorrentino et al. |
| 2010/0057107 A1* | 3/2010 | Sorrentino ......... A61B 17/1285 606/143 |
| 2010/0089970 A1 | 4/2010 | Smith et al. |
| 2010/0121351 A1 | 5/2010 | Whitfield et al. |
| 2010/0137886 A1 | 6/2010 | Zergiebel et al. |
| 2010/0204715 A1 | 8/2010 | Whitfield et al. |
| 2010/0222790 A1 | 9/2010 | Whitfield et al. |
| 2010/0274262 A1 | 10/2010 | Schulz et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0028994 A1 | 2/2011 | Whitfield et al. |
| 2011/0054498 A1 | 3/2011 | Monassevitch et al. |
| 2011/0082474 A1 | 4/2011 | Bindra et al. |
| 2011/0087220 A1 | 4/2011 | Felder et al. |
| 2011/0087241 A1 | 4/2011 | Nguyen |
| 2011/0087242 A1 | 4/2011 | Pribanic |
| 2011/0087243 A1 | 4/2011 | Nguyen et al. |
| 2011/0087268 A1 | 4/2011 | Livneh |
| 2011/0112552 A1 | 5/2011 | Lehman et al. |
| 2011/0137323 A1 | 6/2011 | Malkowski et al. |
| 2011/0137324 A1 | 6/2011 | Boudreaux et al. |
| 2011/0144662 A1 | 6/2011 | McLawhorn et al. |
| 2011/0144665 A1 | 6/2011 | Malkowski |
| 2011/0190791 A1 | 8/2011 | Jacobs et al. |
| 2011/0208211 A1 | 8/2011 | Whitfield et al. |
| 2011/0208212 A1 | 8/2011 | Zergiebel et al. |
| 2011/0218553 A1 | 9/2011 | Huitema et al. |
| 2011/0218554 A1 | 9/2011 | Cheng et al. |
| 2011/0218555 A1 | 9/2011 | Huitema |
| 2011/0218556 A1 | 9/2011 | Nguyen et al. |
| 2011/0224696 A1 | 9/2011 | Huitema et al. |
| 2011/0224700 A1 | 9/2011 | Schmidt et al. |
| 2011/0224701 A1 | 9/2011 | Menn |
| 2011/0230900 A1 | 9/2011 | Sarradon |
| 2011/0245847 A1 | 10/2011 | Menn et al. |
| 2011/0245848 A1 | 10/2011 | Rosenberg et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0029533 A1 | 2/2012 | Whitfield et al. |
| 2012/0029534 A1 | 2/2012 | Whitfield et al. |
| 2012/0041455 A1 | 2/2012 | Martinez |
| 2012/0042497 A1 | 2/2012 | Zergiebel |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0059394 A1 | 3/2012 | Brenner et al. |
| 2012/0065647 A1 | 3/2012 | Litscher et al. |
| 2012/0109158 A1 | 5/2012 | Zammataro |
| 2012/0116420 A1 | 5/2012 | Sorrentino et al. |
| 2012/0123446 A1 | 5/2012 | Aranyi |
| 2012/0197269 A1 | 8/2012 | Zammataro |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0277765 A1 | 11/2012 | Zammataro et al. |
| 2012/0330326 A1 | 12/2012 | Creston et al. |
| 2013/0041379 A1 | 2/2013 | Bodor et al. |
| 2013/0110135 A1 | 5/2013 | Whitfield et al. |
| 2013/0131697 A1 | 5/2013 | Hartoumbekis |
| 2013/0165951 A1 | 6/2013 | Blake, III |
| 2013/0165952 A1 | 6/2013 | Whitfield et al. |
| 2013/0172909 A1 | 7/2013 | Harris |
| 2013/0172910 A1 | 7/2013 | Malkowski |
| 2013/0172911 A1 | 7/2013 | Rockrohr et al. |
| 2013/0172912 A1 | 7/2013 | Whitfield et al. |
| 2013/0175320 A1 | 7/2013 | Mandakolathur Vasudevan et al. |
| 2013/0190779 A1 | 7/2013 | Whitfield |
| 2013/0190780 A1 | 7/2013 | Whitfield et al. |
| 2013/0226200 A1 | 8/2013 | Kappel et al. |
| 2013/0253540 A1 | 9/2013 | Castro et al. |
| 2013/0253541 A1 | 9/2013 | Zergiebel |
| 2013/0274767 A1 | 10/2013 | Sorrentino et al. |
| 2013/0289583 A1 | 10/2013 | Zergiebel et al. |
| 2013/0296891 A1 | 11/2013 | Hartoumbekis |
| 2013/0296892 A1 | 11/2013 | Sorrentino et al. |
| 2013/0310849 A1 | 11/2013 | Malkowski |
| 2013/0325040 A1 | 12/2013 | Zammataro |
| 2013/0325057 A1 | 12/2013 | Larson et al. |
| 2014/0039526 A1 | 2/2014 | Malkowski |
| 2014/0052157 A1 | 2/2014 | Whitfield et al. |
| 2014/0058412 A1 | 2/2014 | Aranyi et al. |
| 2014/0074143 A1 | 3/2014 | Fitzgerald et al. |
| 2014/0188159 A1 | 7/2014 | Steege |
| 2014/0194903 A1 | 7/2014 | Malkowski et al. |
| 2014/0207156 A1 | 7/2014 | Malkowski |
| 2014/0263565 A1 | 9/2014 | Lytle, IV et al. |
| 2014/0276970 A1 | 9/2014 | Messerly et al. |
| 2014/0316441 A1 | 10/2014 | Zergiebel et al. |
| 2014/0330291 A1 | 11/2014 | Whitfield et al. |
| 2014/0371728 A1 | 12/2014 | Vaughn |
| 2015/0005790 A1 | 1/2015 | Whitfield et al. |
| 2015/0032131 A1 | 1/2015 | Sorrentino et al. |
| 2015/0066057 A1 | 3/2015 | Rockrohr et al. |
| 2015/0080916 A1 | 3/2015 | Aranyi et al. |
| 2015/0127022 A1 | 5/2015 | Whitfield et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |

(56) References Cited

U.S. PATENT DOCUMENTS

| | | |
|---|---|---|
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | |
|---|---|---|
| CA | 1163889 A | 3/1984 |
| CN | 100571640 C | 12/2009 |
| CN | 101664329 A | 3/2010 |
| CN | 103251441 A | 8/2013 |
| CN | 104605911 B | 2/2017 |
| DE | 202007003398 U1 | 6/2007 |
| DE | 20 2009 006113 U1 | 7/2009 |
| EP | 0000756 A1 | 2/1979 |
| EP | 0073655 A1 | 3/1983 |
| EP | 0085931 A2 | 8/1983 |
| EP | 0086721 A2 | 8/1983 |
| EP | 0089737 A1 | 9/1983 |
| EP | 0092300 A1 | 10/1983 |
| EP | 0324166 A2 | 7/1989 |
| EP | 0392750 A1 | 10/1990 |
| EP | 0409569 A1 | 1/1991 |
| EP | 0514139 A2 | 11/1992 |
| EP | 0569223 A1 | 11/1993 |
| EP | 0594003 A1 | 4/1994 |
| EP | 0598529 A2 | 5/1994 |
| EP | 0685204 A1 | 12/1995 |
| EP | 0732078 A2 | 9/1996 |
| EP | 0755655 A2 | 1/1997 |
| EP | 0769274 A1 | 4/1997 |
| EP | 0769275 A1 | 4/1997 |
| EP | 0834286 A1 | 4/1998 |
| EP | 1317906 A1 | 6/2003 |
| EP | 1609427 A1 | 12/2005 |
| EP | 1712187 A2 | 10/2006 |
| EP | 1712191 A2 | 10/2006 |
| EP | 1757236 A2 | 2/2007 |
| EP | 1813199 A1 | 8/2007 |
| EP | 1894531 A2 | 3/2008 |
| EP | 1908423 A2 | 4/2008 |
| EP | 1913881 A1 | 4/2008 |
| EP | 1939231 A1 | 7/2008 |
| EP | 2229895 A1 | 9/2010 |
| EP | 2332471 A1 | 6/2011 |
| EP | 2412318 A2 | 2/2012 |
| EP | 3132756 A1 | 2/2017 |
| GB | 2073022 A | 10/1981 |
| JP | 10118083 | 5/1998 |
| JP | 2003033361 A | 2/2003 |
| JP | 2006501954 A | 1/2006 |
| JP | 2006154230 A | 6/2006 |
| JP | 2006209948 A | 8/2006 |
| JP | 2006277221 A | 10/2006 |
| JP | 2007250843 A | 9/2007 |
| JP | 2008017876 A | 1/2008 |
| JP | 2008047498 A | 2/2008 |
| JP | 2008055165 A | 3/2008 |
| JP | 2008515550 A | 5/2008 |
| JP | 2009198991 A | 9/2009 |
| JP | 2011186812 A | 9/2011 |
| JP | 2013166982 A | 8/2013 |
| JP | 5499386 B2 | 5/2014 |
| WO | 9003763 A1 | 4/1990 |
| WO | 0042922 A1 | 7/2000 |
| WO | 0166001 A2 | 9/2001 |
| WO | 0167965 A1 | 9/2001 |
| WO | 03086207 A1 | 10/2003 |
| WO | 03092473 A2 | 11/2003 |
| WO | 2004032762 A1 | 4/2004 |
| WO | 2005091457 A1 | 9/2005 |
| WO | 2006042076 A2 | 4/2006 |
| WO | 2006042084 A2 | 4/2006 |
| WO | 2006042110 A2 | 4/2006 |
| WO | 2006042141 A2 | 4/2006 |
| WO | 2006135479 A2 | 12/2006 |
| WO | 2008118928 A2 | 10/2008 |
| WO | 2008127968 A2 | 10/2008 |
| WO | 2016192096 A1 | 12/2016 |
| WO | 2016192718 A2 | 12/2016 |

(56) References Cited

FOREIGN PATENT DOCUMENTS

| WO | 2016197350 A1 | 12/2016 |
|---|---|---|
| WO | 2016206015 A1 | 12/2016 |
| WO | 2017084000 A1 | 5/2017 |
| WO | 2017146138 A1 | 8/2017 |

OTHER PUBLICATIONS

Extended European Search Report corresponding to EP 11 25 0194.5, completed Nov. 25, 2013 and dated Dec. 3, 2013; (8 pp).
Extended European Search Report corresponding to EP 10 25 1798.4, completed Dec. 12, 2013 and dated Jan. 2, 2014; (9 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
European Office Action corresponding to EP 12 152 989.5 dated May 4, 2015.
Australian Office Action corresponding to AU 2009212759 dated May 7, 2015.
Japanese Office Action corresponding to JP 2013-229070 dated May 8, 2015.
Japanese Office Action corresponding to JP 2013-229996 dated May 8, 2015.
Japanese Office Action corresponding to JP 2014-190735 dated May 27, 2015; no English translation attached—unavailable.
Extended European Search Report corresponding to EP 10 25 2112.7, 2014; completed Jul. 29, 2014 and dated Aug. 5, 2014; (8 pp).
Extended European Search Report corresponding to EP 14 15 1673.2, completed Apr. 25, 2014 and dated May 8, 2014; (8 pp).
The extended European Search Report corresponding to European Application No. EP 07 25 3905.9, completed Jan. 29, 2008; dated Feb. 7, 2008; (7 Pages).
The partial European Search Report corresponding to European Application No. EP 07 25 3807.7, completed Jul. 23, 2008; dated Aug. 1, 2008; (3 pages).
International Search Report corresponding to International Application No. PCT-US08-58185, completed Sep. 4, 2008; dated Sep. 9, 2008; (2 Pages).
The International Search Report corresponding to International Application No. PCT-US08-59859, completed Sep. 14, 2008; dated Sep. 18, 2008; (2 Pages).
The extended European Search Report corresponding to European Application No. EP 07 25 3807.7, completed Nov. 7, 2008; dated Nov. 26, 2008; (11 Pages).
The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).
The extended European Search Report corresponding to European Application No. EP 09 25 2052.7, completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 3, 2010; dated Feb. 5, 2010; (3 Pages).
The extended European Search Report corresponding to European Application No. EP 10 25 0497.4, completed May 1, 2010; dated May 12, 2010; (6 Pages).
The extended European Search Report corresponding to European Application No. EP 10 25 2079.8, completed Mar. 3, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 3, 2011; dated May 20, 2011; (4 pages).
The extended European Search Report corresponding to European Application No. EP 11 00 2681.2, completed May 31, 2011; dated Jun. 10, 2011; (3 Pages).
The extended European Search Report corresponding to European Application No. EP 11 25 0214.1, completed May 25, 2011; dated Jun. 1, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 pages).
The extended European Search Report corresponding to European Application No. EP 12 16 2288.0, completed Jun. 1, 2012 and dated Jul. 7, 2012; (6 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 18 6401.1, completed Nov. 22, 2012 and dated Nov. 30, 2012; (7 Pages).
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.

(56) References Cited

OTHER PUBLICATIONS

Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
International Search Report corresponding to Int'l Patent Appln. PCT/US2018/050316 dated Dec. 31, 2018.
International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
The extended European Search Report corresponding to European Application No. EP 12 19 1706.6, completed Dec. 19, 2012 and dated Jan. 8, 2013; (6 Pages).
"Salute II Disposable Fixation Device", Technique Guide—Laparoscopic and Open Inguinal and Ventral Hernia Repair; Davol, A Bard Company, 2006; (7 Pages).
Extended European Search Report corresponding to EP 12 19 8745.7, completed Mar. 19, 2013 and dated Apr. 11, 2013; (8 pp).
Extended European Search Report corresponding to EP 12 15 2989.5, completed Apr. 9, 2013 and dated Apr. 18, 2013; (9 pp).
Extended European Search Report corresponding to EP 08 73 2820.9, completed Jul. 2, 2013 and dated Jul. 9, 2013; (10 pp).
Extended European Search Report corresponding to EP 12 19 1706.6, completed Dec. 19, 2012 and dated Jan. 8, 2013; (6 pp).
Extended European Search Report corresponding to EP 13 17 2008.8, completed Aug. 14, 2013 and dated Aug. 28, 2013; (8 pp).
European Office Action corresponding to European Appln. No. EP 16 15 9324.9 dated Aug. 7, 2017.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.

* cited by examiner

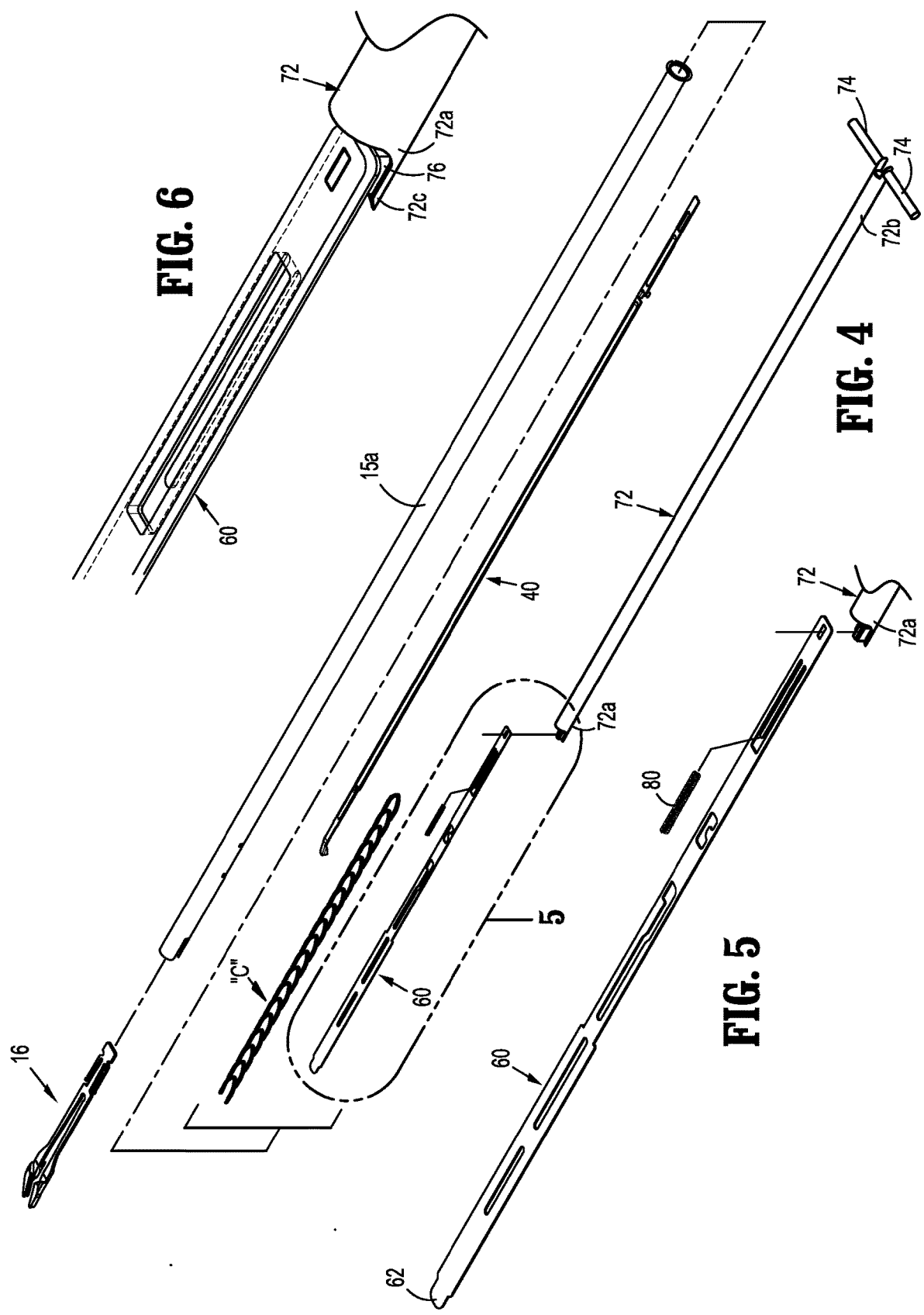

ENDOSCOPIC CLIP APPLIER

CROSS-REFERENCE TO RELATED APPLICATION

The present application is a Continuation application which claims the benefit of and priority to U.S. patent application Ser. No. 15/356,741 filed Nov. 21, 2016, which is a Continuation application which claims the benefit of and priority to U.S. patent application Ser. No. 13/865,412, filed on Apr. 18, 2013, now U.S. Pat. No. 9,532,787, which claims the benefit of and priority to U.S. Provisional Patent Application Ser. No. 61/653,593, filed on May 31, 2012, the entire contents of each of which are incorporated herein by reference.

BACKGROUND

1. Technical Description

The present disclosure relates to surgical clip appliers and, more particularly, to surgical clip appliers including a constant engagement wedge plate and independent manual release.

2. Background of Related Art

Laparoscopic procedures are performed in the interior of the abdomen. These procedures are through a small incision and through a narrow endoscopic tube or cannula inserted through a small entrance incision in the skin. Meanwhile, minimally invasive procedures performed elsewhere in the body are often generally referred to as "endoscopic" procedures. A surgeon will typically insert and extend a tube or cannula device into the body through the entrance incision to provide an access port. This port allows insertion of various surgical instruments therethrough, including endoscopic surgical clip applier.

These instruments are used for performing surgical procedures on organs, blood vessels, ducts, or body tissue far removed from the incision. Often during these procedures, it is necessary to apply hemostatic clips to blood vessels or various ducts to prevent the flow of body fluids therethrough during the procedure. Many different hemostatic clips having different geometries may be used and all are within the scope of the present disclosure.

One advantage of minimally invasive surgical procedures is the reduction of trauma to the patient as a result of accessing internal organs through smaller incisions. Known endoscopic clip appliers have greatly facilitated the advent of more advanced minimally invasive procedures by permitting a number of clip applications during a single entry into the body cavity. Commercially available endoscopic clip appliers are generally of 10 mm outer diameter and are adapted to be introduced through a 10 mm cannula. Other commercially available endoscopic clip appliers may also be generally have a 5 mm outer diameter and are adapted to be introduced through a 5 mm cannula.

In order for a 5 mm clip applier to be able to pass through a 5 mm cannula, it may be necessary for the jaws of the clip applier to deflect closed or be held in a closed state during insertion. However, following insertion, it is desirable for the jaws of the 5 mm clip applier to return to a fully opened condition and, preferably be held in the fully open condition, during manipulation in the anatomical cavity, so that the jaws may retain their alignment with one another and so that the jaws may proper receive a surgical clip therein for formation, as needed.

Accordingly, a need exists for a surgical clip applier including a mechanism for supporting the pair of jaws at substantially all times except during an insertion/retraction of the surgical clip applier to the anatomical cavity, and during a firing of the surgical clip applier.

Accordingly, a need also exists for a surgical clip applier including a pair of jaws that may be held in a fully open condition, during manipulation in the anatomical cavity, and which may be selectively approximated for insertion through a 5 mm cannula.

SUMMARY

According to the present disclosure, a surgical clip applier including a constant engagement wedge plate and independent manual release is provided.

According to an aspect of the present disclosure, an endoscopic surgical clip applier for application of surgical clips to body tissue, is provided, wherein a distal end of the surgical clip applier is introduced to a target surgical site through a cannula having a fixed diameter lumen. The surgical clip applier comprises a handle assembly including a trigger actuatable to actuate the surgical clip applier; and an endoscopic portion supported by and extending from the handle assembly. The endoscopic portion includes an outer tube having a diameter dimensioned for passage through the lumen of the cannula; a pair of jaws supported at a distal end of the outer tube, wherein the pair of jaws are movable between a fully open condition and approximated conditions, wherein when the pair of jaws are in the fully open condition the pair of jaws extend radially beyond an outer diameter of the outer tube to a dimension greater than the fixed diameter of the lumen of the cannula; and when the pair of jaws are in at least one approximated condition the pair of jaws have a transverse dimension permitting passage through the lumen of the cannula.

The endoscopic portion also includes a wedge plate slidably disposed within the endoscopic portion, the wedge plate defining a nose at a distal end thereof. The wedge plate is movable between a distal-most position wherein the nose is interposed between the pair of jaws to maintain the pair of jaws in the fully open condition; and at least one proximal position wherein the nose is at least partially withdrawn from between the pair of jaws to permit the pair of jaws to be placed in the at least one approximated condition.

The surgical clip also includes a release mechanism connected to the wedge plate. In use, an actuation of the release mechanism withdraws the nose of the wedge plate from between the pair of jaws. Also in use, an actuation of the trigger withdraws the nose from between the pair of jaws.

According to another aspect of the present disclosure, an endoscopic surgical clip applier for application of surgical clips to body tissue, is provided, wherein a distal end of the surgical clip applier is introduced to a target surgical site through a cannula having a fixed diameter lumen. The surgical clip applier comprises a handle assembly including a trigger, the trigger being actuatable to actuate the surgical clip applier; and an endoscopic portion supported by and extending from the handle assembly.

The endoscopic portion includes an outer tube having a diameter dimensioned for passage through the lumen of the cannula; and a pair of jaws supported at a distal end of the outer tube, wherein the pair of jaws is movable between a fully open condition and approximated conditions. Wherein when the pair of jaws are in the fully open condition the pair of jaws extend radially beyond an outer diameter of the outer tube to a dimension greater than the fixed diameter of the lumen of the cannula; and when the pair of jaws are in at least one approximated condition the pair of jaws have a transverse dimension at least less than the fixed diameter of the lumen of the cannula. The endoscopic portion also includes a wedge plate slidably disposed within at least the endoscopic portion, wherein the wedge plate defines a distal end. The wedge plate is movable between a distal-most position wherein the distal end of the wedge plate is interposed between the pair of jaws to maintain the pair of jaws in the fully open condition; and at least one proximal position wherein the distal end of the wedge plate is at least partially withdrawn from between the pair of jaws to permit the pair of jaws to be placed in at least a partially approximated condition.

The surgical clip applier further includes a release mechanism connected to the wedge plate. In use, an actuation of the release mechanism withdraws the distal end of the wedge plate from between the pair of jaws. Also in use, an actuation of the trigger withdraws the distal end of the wedge plate from between the pair of jaws.

The release mechanism may include a biasing member for urging the wedge plate to the distal-most position. The biasing member may be connected to at least the wedge plate.

The release mechanism may include an inner tube slidably disposed within the outer tube, wherein the inner tube includes a distal end coupled to the wedge plate.

A proximal end of the inner tube may extend into the handle assembly. The release mechanism may include at least one release pin extending from the proximal end of the inner tube through a respective slot defined in the handle assembly.

The wedge plate may be in the distal-most position when the trigger is in an un-actuated condition.

The wedge plate may be in the distal-most position when the trigger and the release mechanism are both in an un-actuate condition.

The wedge plate may be at least partially withdrawn when the trigger is at least partially actuated.

The withdrawal of the wedge plate by the trigger may be independent of the withdrawal of the wedge plate by the release mechanism.

The surgical clip applier may further include at least one surgical clip loaded therein.

The surgical clip applier may further comprise a clip pusher configured to individually distally advance a surgical clip to the pair of jaws while the pair of jaws are in the open condition.

The surgical clip applier may further include a jaw closure member positioned adjacent the pair of jaws to move the pair of jaws to an approximated position upon an actuation of the trigger.

BRIEF DESCRIPTION OF THE DRAWINGS

The present clip applier will be more fully appreciated as the same becomes better understood from the following detailed description when considered in connection with the following drawings, in which:

FIG. 4 is a perspective view, with parts separated, of components of an endoscopic portion and a manual release mechanism of the surgical clip applier of FIGS. 1-3;

FIG. 5 is an enlarged perspective view of the indicated area of detail of FIG. 4;

FIG. 6 is an enlarged perspective view illustrating a connection between a distal end of a manual release mechanism and a proximal end of a wedge plate;

DETAILED DESCRIPTION OF THE EMBODIMENTS

Figure 1:
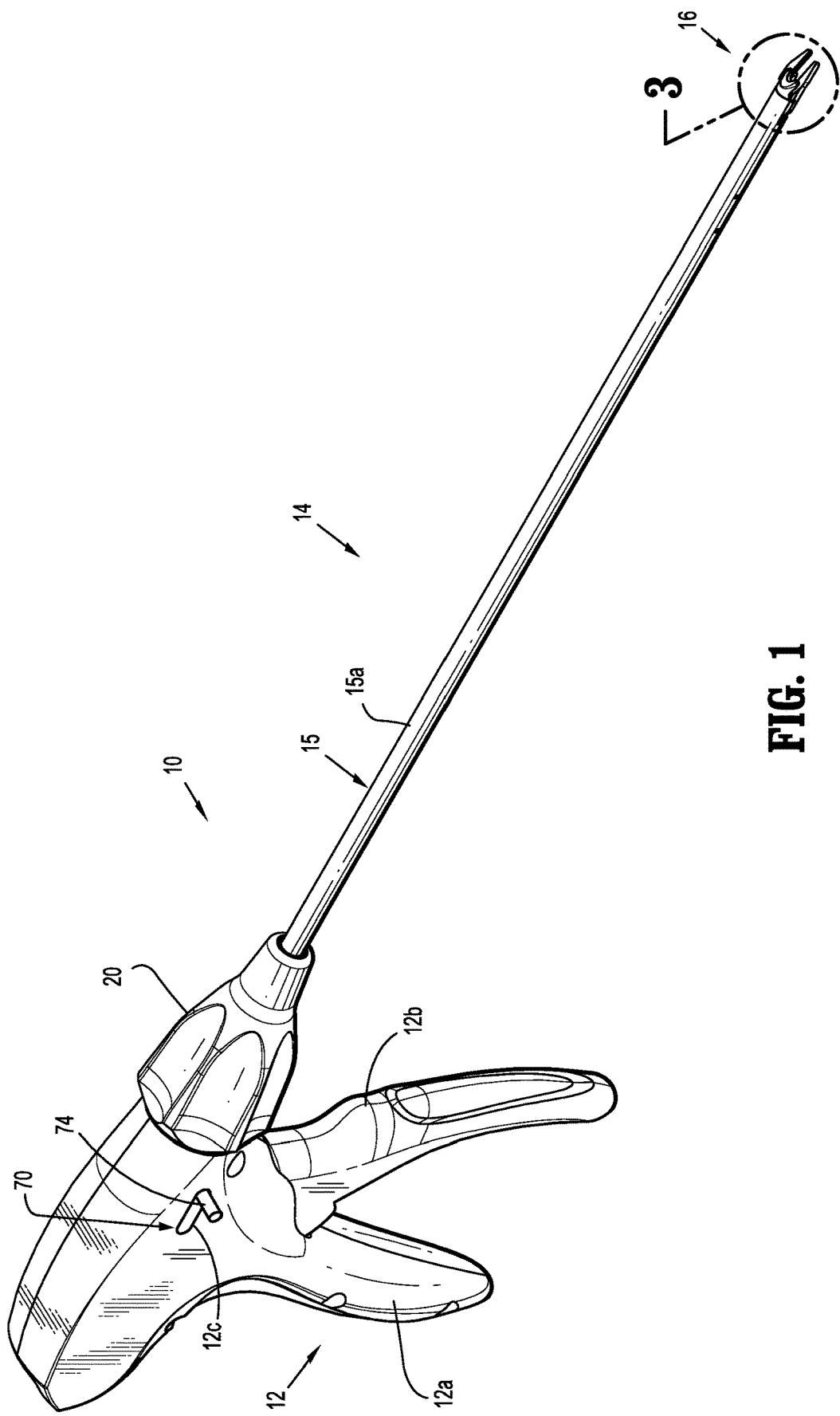
FIG. 1 is a distal, right side, perspective view of a surgical clip applier according to an embodiment of the present disclosure, shown in a first condition.

Embodiments of surgical clip appliers in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Figure 2:
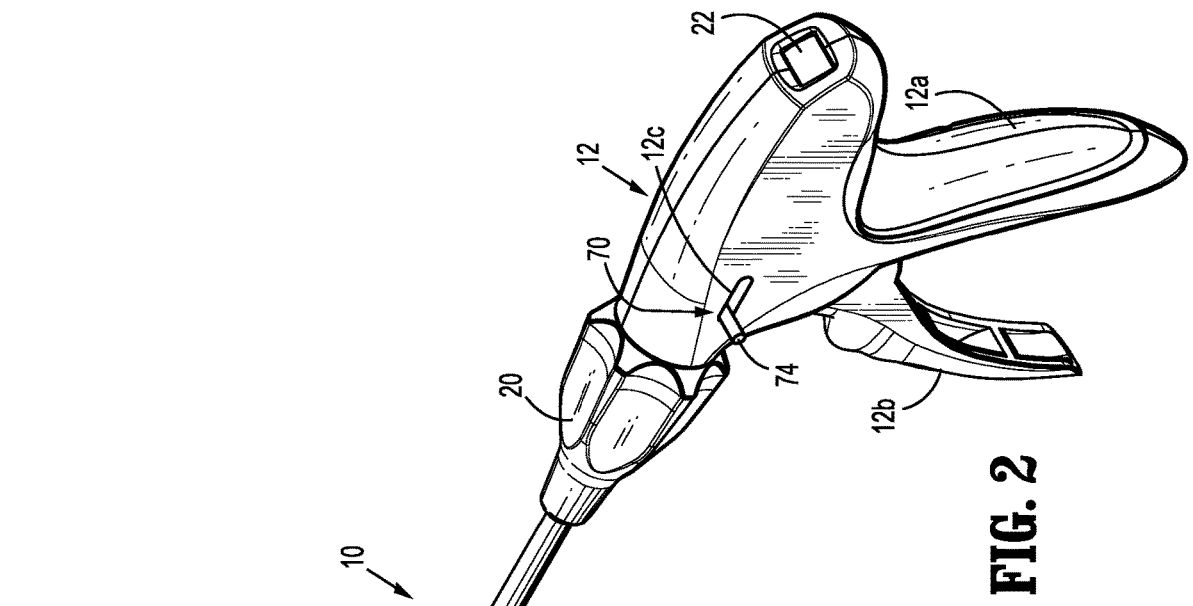
FIG. 2 is a proximal, left side, perspective view of the surgical clip applier of FIG. 1.
Figure 3:
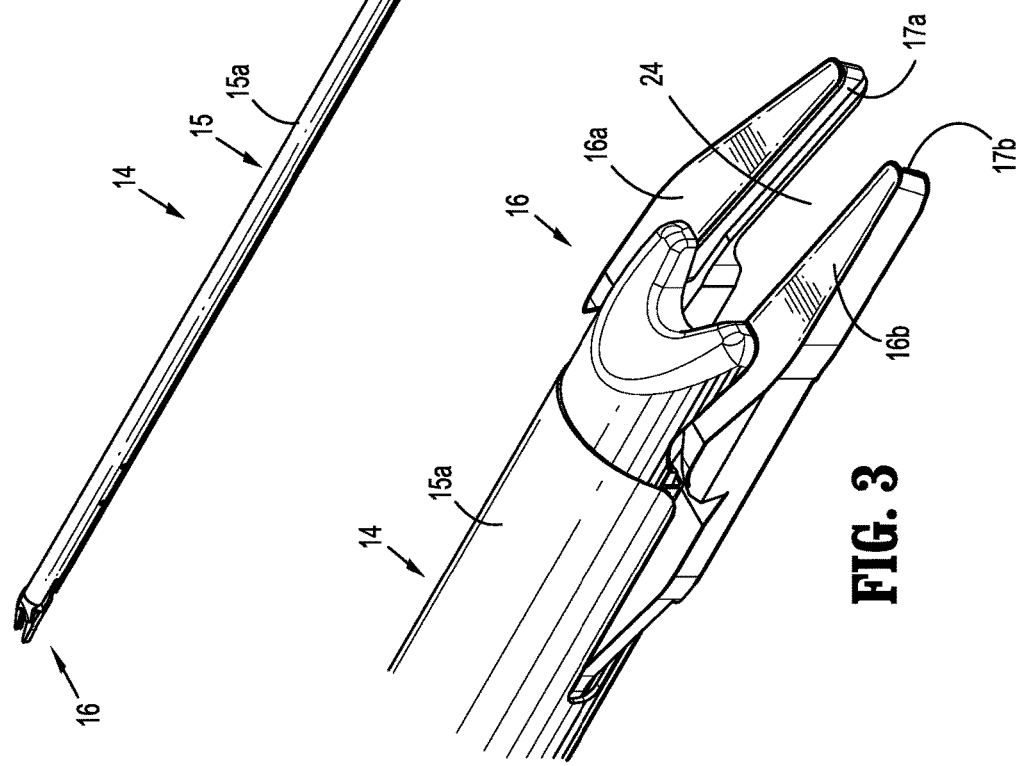
FIG. 3 is an enlarged view of the indicated area of detail of FIG. 1.
Figure 7:
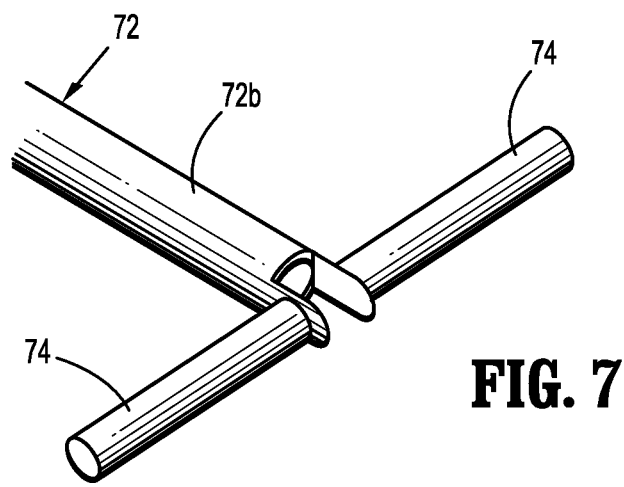
FIG. 7 is a perspective view of a proximal end of the release mechanism illustrated in FIG. 4.
Figure 8:
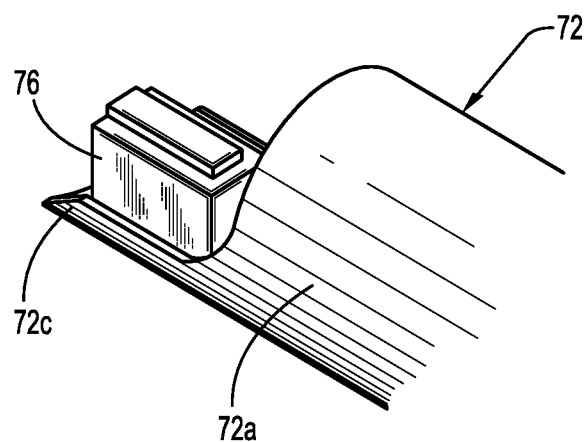
FIG. 8 is a perspective view of a distal end of the release mechanism illustrated in FIG. 4.

Referring now to FIGS. 1-3, a surgical clip applier, in accordance with an embodiment of the present disclosure, is generally designated with numeral 10. Surgical clip applier 10 includes a handle assembly 12 and an endoscopic portion 14 supported by and extending distally from handle assembly 12. Handle assembly 12 is made from a thermoplastic material and the elongated member is made from a biocompatible material (e.g., a stainless steel or a titanium material or alloy).

Handle assembly 12 of clip applier 10 includes a fixed handle 12*a* and a trigger 12*b* operatively connected to fixed handle 12*a*.

Endoscopic portion 14 of clip applier 10 includes an elongated tubular member 15, supported by and extending from handle assembly 12, and a pair of jaws 16 mounted on a distal end of tubular member 15. The pair of jaws 16 are formed from a suitable biocompatible material, such as, for example, stainless steel, titanium or a suitable alloy. In use, complete actuation and release of trigger 12b results in a complete closing and opening of the pair of jaws 16.

The pair of jaws 16 includes a first jaw member 16a and a second jaw member 16b disposed in juxtaposed, planar relation to one another. Each jaw member 16a, 16b defines a respective clip channel 17a, 17b formed in opposed surfaces thereof for receiving an unformed surgical clip "C" therein, and for retaining the surgical clip "C" during an approximation or closing of the jaw members 16a, 16b to form the surgical clip "C".

Endoscopic portion 14 of clip applier 10 includes a rotation knob 20. Knob 20 is rotatably mounted on a distal end of handle assembly 12 and is connected to the elongated tubular member 15 to provide a three hundred sixty degree (360°) rotation of the elongated tubular member 15 and the pair of jaws 16 thereon relative to a longitudinal center axis of endoscopic portion 14.

Endoscopic portion 14 of clip applier 10 includes a clip pusher feed bar 40 for feeding and/or advancing individual surgical clips "C" between jaw members 16a, 16b of the pair of jaws 16. Feed bar 40 is operatively connected to and actuatable by trigger 12b as trigger 12b is actuated.

Reference may be made to U.S. Pat. No. 7,819,886, the entire content of which is incorporated herein by reference, for a detailed discussion of the construction and configuration of many of the components of surgical clip applier 10, and some of the operation of said components of surgical clip applier 10.

Tubular member 15 of endoscopic portion 14 of clip applier 10 includes an outer tube 15a configured to support the pair of jaws 16 at a distal end thereof and a number of other operative components of surgical clip applier 10. Typically, the pairs of jaws 16, when in a fully open or un-approximated condition, extend radially outward from or beyond an outer surface of the outer tube 15a.

Outer tube 15a defines an outer diameter that generally constitutes or defines the size of the surgical clip applier 10, e.g., 5 mm, 10 mm, etc. As mentioned above, surgical clip appliers 10 are introduced to an anatomical space via a cannula 100 (see FIGS. 9 and 13) defining a lumen 102 therethrough, wherein the lumen 102 of the cannula 100 defines an inner diameter or transverse dimension "d". Generally, in use, the cannula 100 selected for the surgical procedure must accommodate the size (i.e., diameter) of the surgical clip applier that is to be inserted therethrough, wherein the surgical clip applier has a maximum transverse dimension or is approximately equal to, and smaller, than the inner diameter "d" of lumen 102 of cannula 100. For example, a 5 mm clip applier will typically necessitate the use of a cannula 100 having a lumen 102 of at least 5 mm.

Since the lumen 102 of the cannula 100 can only accommodate a fixed dimension, and since the pairs of jaws 16, when in a fully open or un-approximated condition, extend radially outward from or beyond an outer surface of the outer tube 15a, to a dimension "D" (see FIG. 9), the pair of jaws 16 may deflect radially inward or may be approximated, prior to or during passage through the lumen 102 of the cannula 100, and then permitted to return to or actuated to a fully open condition after passage through the lumen 102 of the cannula 100.

Surgical clip applier 10 includes a wedge plate 60 slidably disposed within at least endoscopic portion 14 and which is actuatable, directly or indirectly, by trigger 12b. Wedge plate 60 includes a nose 62 formed at a distal end thereof. In accordance with the present disclosure, wedge plate 60 includes a distal-most position, wherein nose 62 of wedge plate 60 is interposed between first jaw member 16a and second jaw member 16b of the pair of jaws 16. When in the distal-most position, as seen in FIGS. 9 and 10, wedge plate 60, and nose 62 thereof, functions to support the pair of jaws 16, to spread the pair of jaws 16 to properly receive a new or un-formed surgical clip "C" therein, and to help maintain first jaw member 16a and second jaw member 16b of the pair of jaws 16 in proper juxtaposed alignment with one another.

Figure 13:
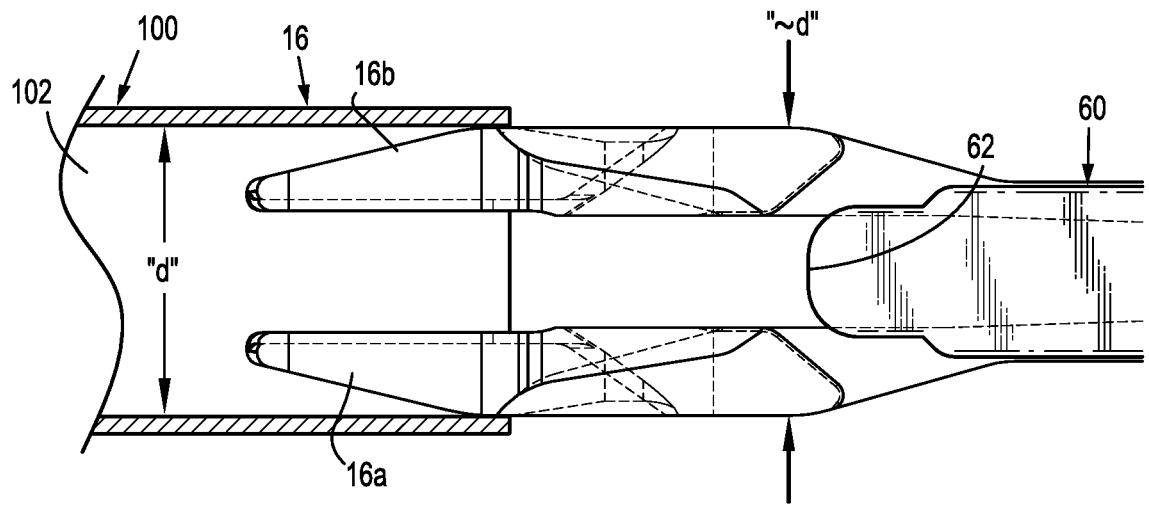
FIG. 13 is a top, plan view of a pair of jaws of the surgical clip applier of FIGS. 1-3, shown in a second condition, illustrating the pair of jaws having a transverse dimension that is less than a transverse dimension of the lumen of the cannula, thereby permitting entrance of the pair of jaws.
Figure 14:
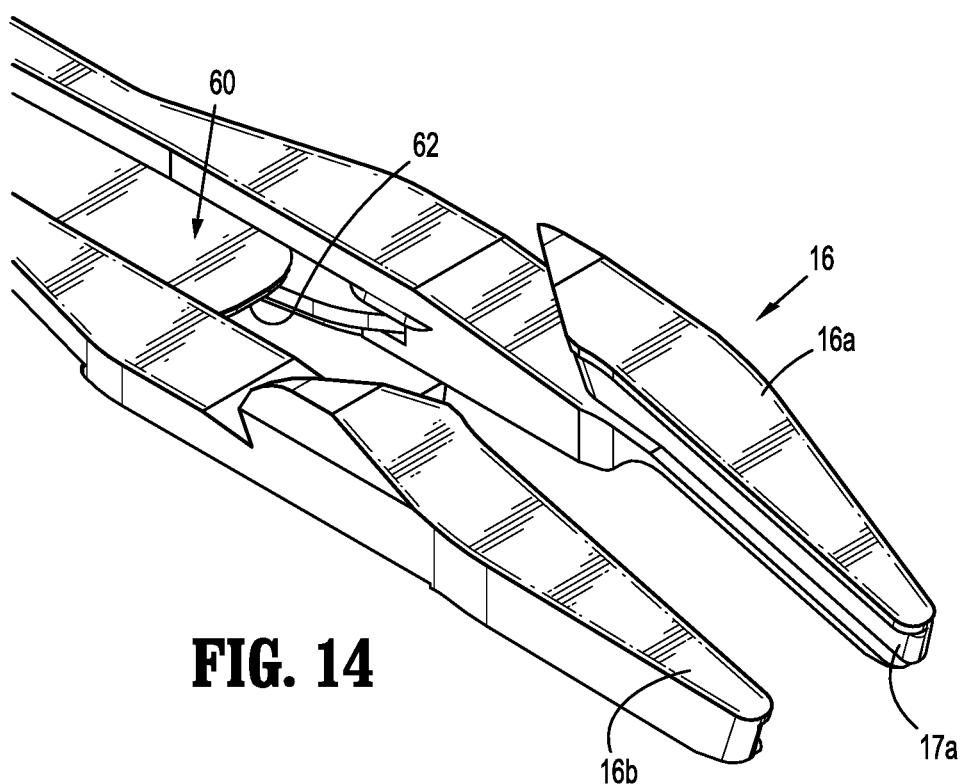
FIG. 14 is a top, perspective view of the pair of jaws of FIG. 13.
Figure 15:
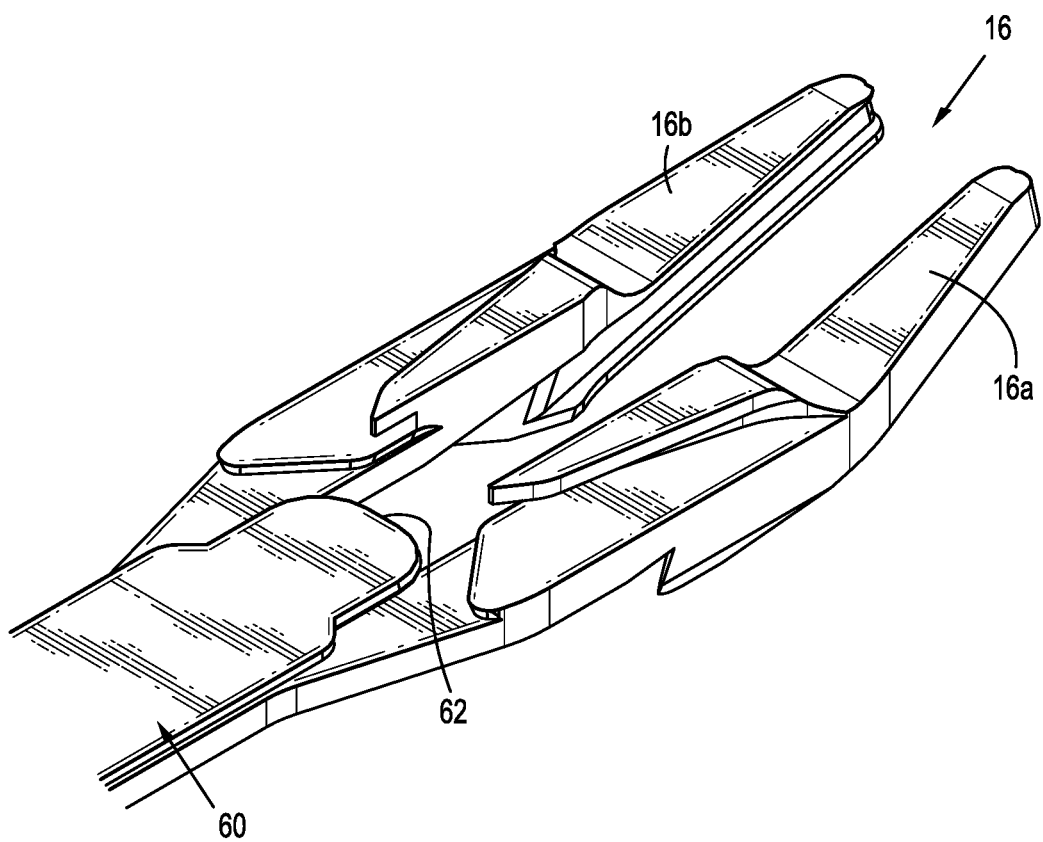
FIG. 15 is a bottom, perspective view of the pair of jaws of FIGS. 13 and 14.

Also in accordance with the present disclosure, wedge plate 60 includes at least one proximal position, as seen in FIGS. 13-15, wherein nose 62 of wedge plate 60 is removed from between first jaw member 16a and second jaw member 16b of the pair of jaws 16. When in any proximal position, wedge plate 60, and nose 62 thereof, does not affect a closing of the pair of jaws 16 and thus the pair of jaws 16 is free to approximate or close to form any surgical clip "C" disposed between first jaw member 16a and second jaw member 16b.

Figure 9:
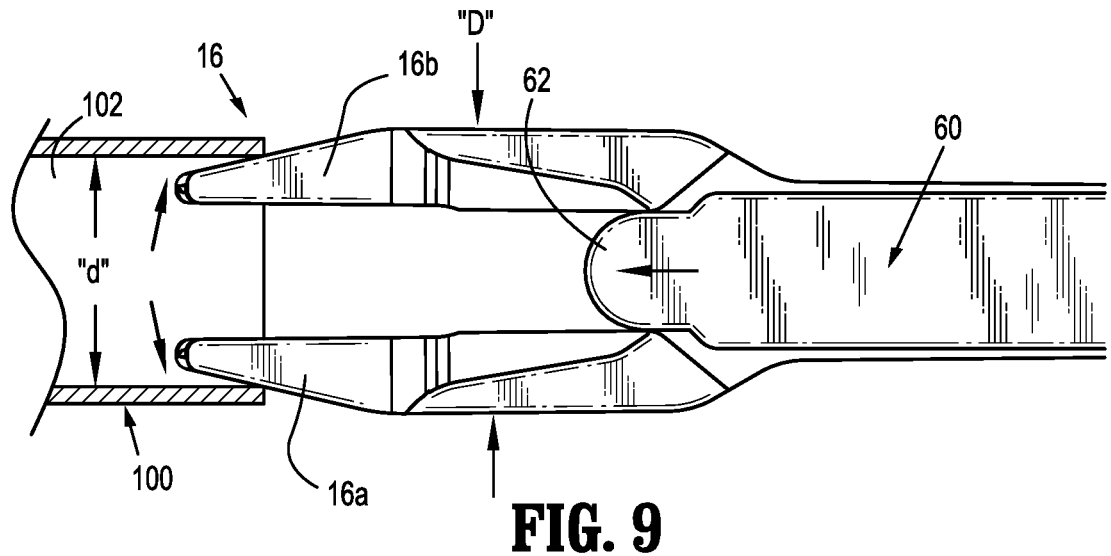
FIG. 9 is a bottom, plan view of a pair of jaws of the surgical clip applier of FIGS. 1-3, shown in a first condition, illustrating the pair of jaws having a transverse dimension that is greater than a transverse dimension of a lumen of a cannula, thereby preventing entrance of the pair of jaws.
Figure 10:
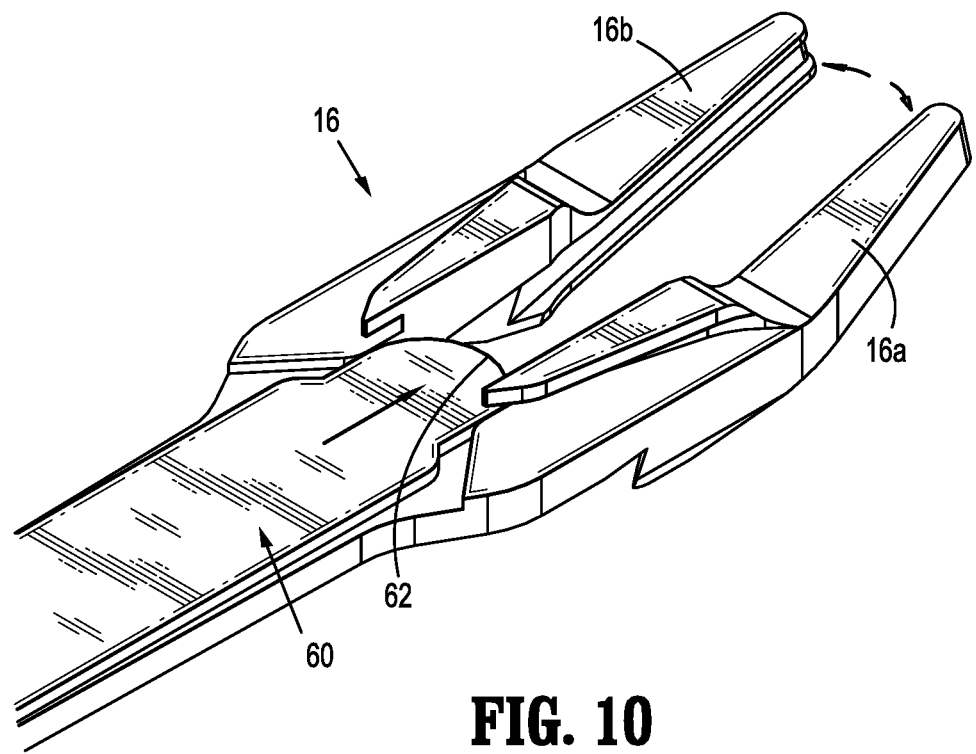
FIG. 10 is a bottom, perspective view of the pair of jaws of FIG. 9.

In accordance with the present disclosure, when clip applier 10 is in an initial or un-actuated condition, trigger 12b is in an initial or un-actuated condition, and wedge plate 60 is in a distal-most position such that nose 62 thereof is disposed between the pair of jaws 16 to maintain the pair of jaws 60 in a fully opened condition (see FIGS. 9 and 10). During use, as trigger 12b is actuated from the initial or un-actuated condition, to any subsequent or actuated condition, trigger 12b directly or indirectly causes wedge plate 60 to retract to withdraw nose 62 thereof from between first jaw member 16a and second jaw member 16b (see FIGS. 13-15), to allow for the pair of jaws 16 to approximate and form a surgical clip "C" disposed between first jaw member 16a and second jaw member 16b.

With reference back to FIGS. 9 and 10, with nose 62 of wedge plate 60 disposed between first jaw member 16a and second jaw member 16b, the pair of jaws 16 are maintained in a fully open or un-approximated condition. In accordance with the present disclosure, as mentioned above, when the pair of jaws 16 is in the fully open or un-approximated condition, the pair of jaws 16 project beyond or extend radially outward from an outer surface of the outer tube 15a, to have a transverse dimension "D".

Further, with nose 62 of wedge plate 60 withdrawn from between first jaw member 16a and second jaw member 16b, the pair of jaws 16 is capable of being approximated so that the first jaw member 16a and the second jaw member 16b do not extend radially beyond an outer bounds or exterior surface of outer tube 15a of endoscopic portion 14 (i.e., the pair of jaws 16 has a transverse dimension "~d" which is smaller than the outer diameter of outer tube 15a of endoscopic portion 14 and approximately equal to, and smaller, than the inner dimension "d" of the lumen 102 of cannula 100).

In accordance with the present disclosure, as seen throughout the figures, and particularly as seen in FIGS. 1-8, 11 and 12, surgical clip applier 10 includes a manual release mechanism 70 for wedge plate 60 that is configured and adapted to withdrawn wedge plate 60, from its distal-most position, independently of any direct or indirect withdrawal of wedge plate 60 due to the actuation of trigger 12b.

Manual release mechanism 70 includes an inner tube 72 (or rigid bar member or the like) slidably disposed within outer tube 15a. Inner tube 72 includes a distal end 72a disposed and extending into endoscopic portion 14, and a proximal end 72b disposed within handle assembly 12. As seen in FIGS. 1, 2, 4 and 7, inner tube 72 includes at least one retraction pin 74 supported thereon and extending from proximal end 72b and preferably projecting through an elongate slot 12c defined in fixed handle 12a. Desirably, a pair of retraction pins 74 supported on inner tube 72 and projecting through respective elongate slots 12c of fixed handle 12a.

As seen in FIGS. 4-6 and 8, inner tube 72 includes a lip or flange 72c extending distally from distal end 72a. Inner tube 72 includes an attachment block 76 connected to and supported on flange 72c.

Surgical clip applier 10 may include a link member 78 secured to wedge plate 60, wherein link member 78 provides reinforcement and support to a proximal end of wedge plate 60. Link member 78 may be configured to engage or be coupled to attachment block 76 as well. In this manner, as inner tube 72 is actuated, to move wedge plate 60, attachment block 76 acts on both wedge plate 60 and link member 78 to move wedge plate 60.

Manual release mechanism 70 may include a biasing member 80, in the form of a coil spring or the like, connected to wedge plate 60 and/or link member 78 and to a fixed structure or boss (not shown) provided in handle assembly 12 and/or endoscopic portion 14. Biasing member 80 is configured and attached in such a manner so as to draw wedge plate 60 to the distal-most position, wherein nose 62 is disposed between the pair of jaws 16, as described above, and so as to draw inner tube 72 to a distal-most position. In accordance with the present disclosure, it is further contemplated that biasing member 80 may be connected to inner tube 72 in such a manner so as to move inner tube 72 to the distal-most position, whereby wedge plate 60 is pushed by inner tube 72 to the distal-most position such that nose 62 of wedge plate 60 is disposed between the pair of jaws 16 and inner tube 72 is disposed in a distal-most position.

Figure 11:
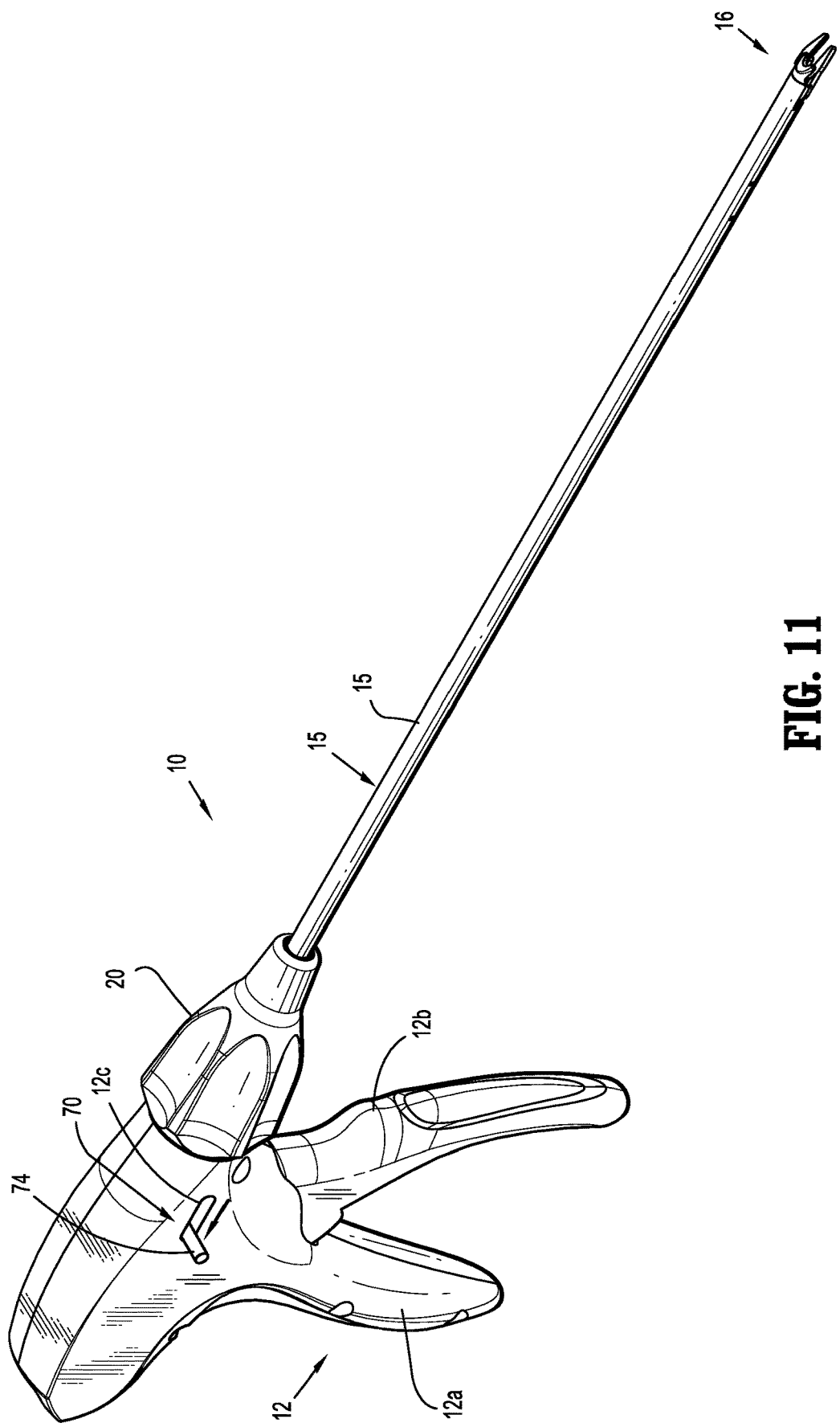
FIG. 11 is a distal, right side, perspective view of the surgical clip applier of FIGS. 1-3, shown in a second condition.
Figure 12:
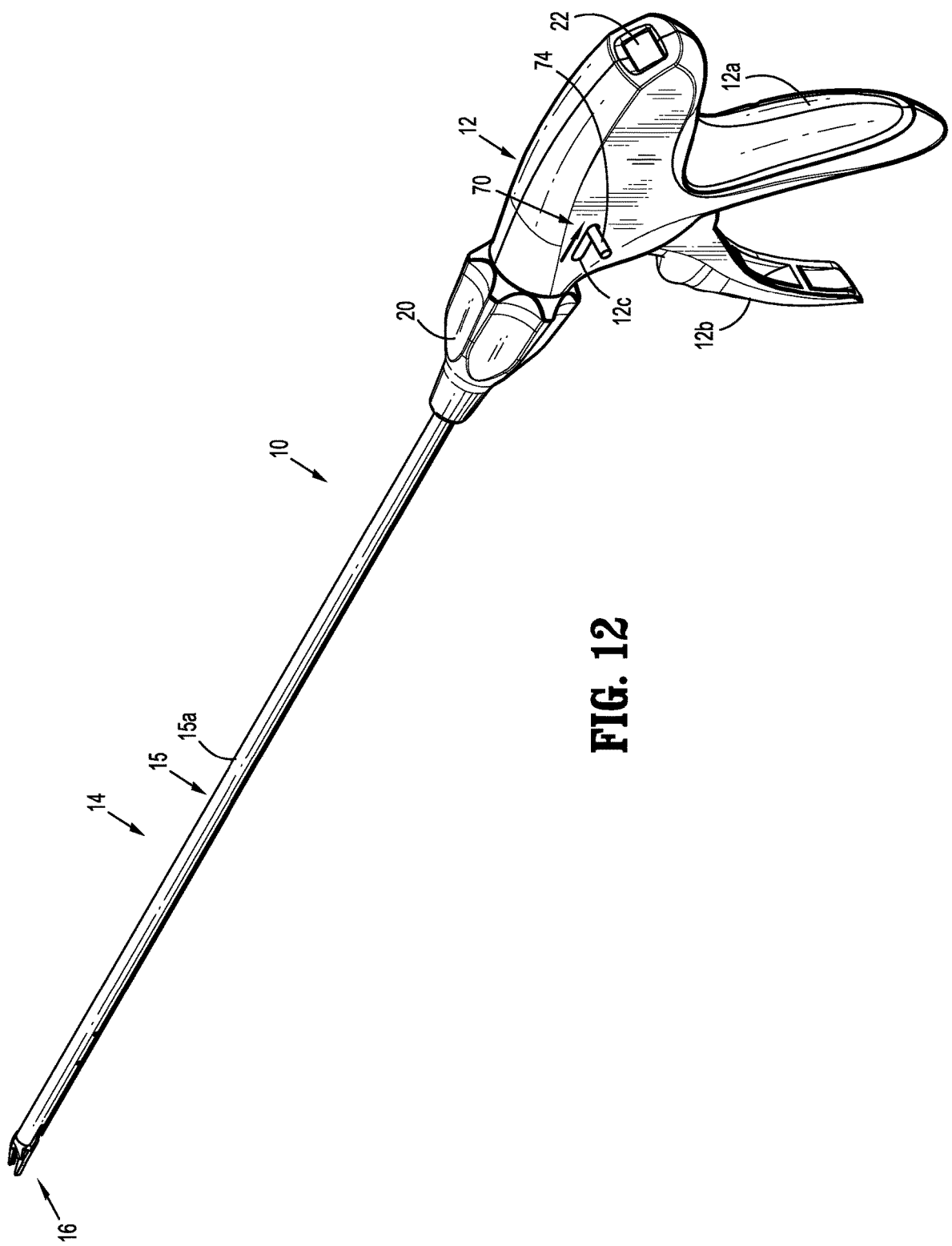
FIG. 12 is a proximal, left side, perspective view of the surgical clip applier of FIG. 11.

In operation, independent of the actuation of surgical clip applier 10 by trigger 12b, wedge plate 60 may be actuated or moved from the distal-most position thereof to any proximal position upon the actuation of inner tube 72 from a distal-most position thereof to any proximal position thereof. In particular, with wedge plate 60 and inner tube 72 at a distal-most position (see FIGS. 1-3, 9 and 10), as seen in FIGS. 11 and 12, a user may withdraw inner tube 72 to a proximal position by moving retraction pin(s) 74 in a proximal direction relative to handle assembly 12. As inner tube 72 is moved or withdrawn in a proximal direction, inner tube 72 act on wedge plate 60 (and optionally link member 78) to move of withdraw wedge plate 60 in a proximal direction to a proximal position. As discussed above, when wedge plate 60 is moved to a proximal position, nose 62 thereof with withdrawn from between the pair of jaws 16, as seen in FIGS. 13-15, thus allowing or freeing the pair of jaws 16 to close.

Also in use, as inner tube 72 and wedge plate 60 are withdrawn, biasing member 80 is acted upon to create a potential energy therewith, such as, for example, by stretching or compressing biasing member 80.

Following withdrawal of inner tube 72 and wedge plate 60, when desired or necessary, the user may release retraction pin(s) 74, thereby permitting the potential energy of the biasing member 80 to return the biasing member 80 to its original condition (i.e., to contract or expand). As biasing member 80 returns to its original condition, biasing member 80 moves inner tube 72 and wedge plate 60 to their distal-most positions, wherein nose 62 of wedge plate 60 is re-introduced between the pair of jaws 16 so as to urge the pair of jaws 16 to their spaced apart or fully open position, as seen in FIGS. 9 and 10.

In accordance with the present disclosure, since the pair of jaws 16 extend radially outward from or beyond an outer surface of the outer tube 15a, when in a fully open or un-approximated condition, in order to pass a distal end of surgical clip applier 10 through the fixed diameter of the lumen 102 of the cannula 100, the manual release mechanism 70 is actuated, as described above and shown in FIGS. 11 and 12, to withdraw nose 62 of wedge plate 60 from between the pair of jaws 16, as shown in FIGS. 13-15. With nose 62 of wedge plate 60 withdrawn from between the pair of jaws 16, the pair of jaws 16 are free to approximate relative to one another. In this manner, as seen in FIG. 13, as the distal end of the surgical clip applier 10 (including the pair of jaws 16) is inserted into and passed through the lumen 102 of the cannula 100, the pair of jaws 16 are acted on by an inner surface of the lumen 102 of the cannula 100, causing the pair of jaws 16 to deflect inward (toward one another by an amount sufficient for the transverse dimension of the pair of jaws 16 to be reduced by an amount sufficient to enter the fixed diameter lumen of the cannula 100) until the pair of jaws 16 completely traverse the lumen 102 of the cannula 100 and exit from a distal end of the lumen 102 of the cannula 100.

Once the pair of jaws 16 completely traverse the lumen 102 of the cannula 100 and exit from a distal end of the lumen 102 of the cannula 100, a natural resiliency of the pair of jaws 16 will tend to cause the pair of jaws 16 to at least partially spread. Additionally, following complete passage of the pair of jaws 16 beyond a distal end of the lumen 102 of the cannula 100, the user releases manual release mechanism 70, as described above, in order to re-introduce nose 62 of wedge plate 60 between the pair of jaws 16 and return the pair of jaws 16 to the fully open condition, as described above.

Thereafter, the surgical clip applier 10 may be used in a normal manner to load and form surgical clips "C" on underlying vessels by actuating and re-actuating trigger 12b.

Also thereafter, in order to withdraw surgical clip applier 10 from within the cannula 100, following the surgical procedure or following an application of all of the surgical clips "C" loaded within the surgical clip applier 10, the manual release mechanism 70 may once again be actuated, as described above, to withdraw nose 62 of wedge plate 60 from between the pair of jaws 16, to permit and/or free the pair of jaws 16 to deflect inward for re-passage through the lumen 102 of the cannula 100.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. An endoscopic surgical clip applier for application of surgical clips to body tissue, the surgical clip applier comprising:
   a handle assembly including a trigger actuatable to actuate the surgical clip applier;
   an endoscopic portion supported by and extending from the handle assembly, the endoscopic portion including:
      an outer tube;

a pair of jaws supported at a distal end of the outer tube, wherein the pair of jaws are movable between a fully opened condition and at least one approximated condition;

a wedge plate slidably disposed within the endoscopic portion, the wedge plate defining a nose at a distal end thereof, wherein the wedge plate is movable between:
- a distal-most position wherein the nose is interposed between the pair of jaws to maintain the pair of jaws in the fully opened condition; and
- at least one proximal position wherein the nose of the wedge plate is at least partially withdrawn from between the pair of jaws to permit the pair of jaws to be placed in the at least one approximated condition; and a release mechanism connected to the wedge plate, the release mechanism slidably disposed within the outer tube and selectively directly actuatable from an exterior of the handle assembly, the release mechanism including a distal end coupled to the wedge plate and a proximal end projecting from within the handle assembly, wherein an actuation of the release mechanism withdraws the nose of the wedge plate at least partially from between the pair of jaws; and wherein an actuation of the trigger withdraws the nose of the wedge plate at least partially from between the pair of jaws.

2. The endoscopic surgical clip applier according to claim 1, wherein actuation of the trigger completely withdraws the nose of the wedge plate from between the pair of jaws.

3. The endoscopic surgical clip applier according to claim 2, wherein the nose of the wedge plate is interposed between the pair of jaws when the trigger is in an un-actuated position.

4. The endoscopic surgical clip applier according to claim 1, wherein the endoscopic assembly includes a biasing member operatively coupled to the wedge plate, the biasing member configured for urging the wedge plate towards a position wherein the nose thereof is interposed between the pair of jaws.

5. The endoscopic surgical clip applier according to claim 1, wherein the release mechanism of the endoscopic assembly includes an inner shaft having a distal end portion operatively coupled to the wedge plate and a proximal end portion disposed in the handle assembly, the proximal end portion of the inner shaft being accessible through the handle assembly to actuate the release mechanism.

6. The endoscopic surgical clip applier according to claim 5, wherein the proximal end portion of the inner shaft includes an actuation member, the actuation member extending from the proximal end portion of the inner shaft and through a respective slot defined in the handle assembly, the actuation member configured for actuating the inner shaft between:
- a first position wherein the nose of the wedge plate is interposed between the pair of jaws; and
- a second position wherein the nose of the wedge plate is withdrawn from between the pair of jaws, wherein actuation of the inner shaft is independent of actuation of the trigger.

7. The endoscopic surgical clip applier according to claim 6, wherein the nose of the wedge plate is interposed between the pair of jaws when the trigger is in the un-actuated position and the inner shaft is in the first position.

8. The endoscopic surgical clip applier according to claim 6, wherein the nose of the wedge plate is withdrawn from between the pair of jaws when the trigger is in the un-actuated position and the inner shaft is in the second position.

9. The endoscopic surgical clip applier according to claim 5, wherein the distal end portion of the inner shaft includes an attachment block and a proximal end portion of the wedge plate includes an attachment slot configured to receive the attachment block of the inner shaft to operatively couple the wedge plate and the inner shaft.

10. The endoscopic surgical clip applier according to claim 1, wherein the endoscopic assembly includes a link member secured to the wedge plate, the link member configured for reinforcing the proximal end portion of the wedge plate.

11. The endoscopic surgical clip applier according to claim 1, wherein the endoscopic assembly includes:
- a channel defined in the outer tube;
- at least one surgical clip disposed within the channel of the outer tube; and
- a clip pusher configured to individually, distally advance the at least one surgical clip towards the pair of jaws while the pair of jaws are in the fully opened condition.

12. The endoscopic surgical clip applier according to claim 1, wherein the outer tube has an outer diameter, and wherein when the pair of jaws are in the fully opened condition the pair of jaws extend radially beyond the outer diameter of the outer tube; and when the pair of jaws are in the at least one approximated condition the pair of jaws have a transverse dimension equal to or less than the outer diameter of the outer tube.

13. An endoscopic surgical clip applier for application of surgical clips to body tissue, the surgical clip applier comprising:
an endoscopic portion including:
- an outer tube defining an outer diameter;
- a pair of jaws supported at a distal end of the outer tube, wherein the pair of jaws are movable between a fully opened condition and at least one approximated condition;
- a wedge plate slidably disposed within the endoscopic portion, the wedge plate defining a nose at a distal end thereof, wherein the wedge plate is movable between:
  - a distal-most position wherein the nose is interposed between the pair of jaws to maintain the pair of jaws in the fully opened condition; and
  - at least one proximal position wherein the nose of the wedge plate is at least partially withdrawn from between the pair of jaws to permit the pair of jaws to be placed in the at least one approximated condition; and
- a release mechanism connected to the wedge plate, the release mechanism slidably disposed within the outer tube and selectively directly actuatable from an exterior of the surgical clip applier, the release mechanism including a distal end coupled to the wedge plate and a proximal end projecting from within the surgical clip applier, wherein an actuation of the release mechanism withdraws the nose of the wedge plate at least partially from between the pair of jaws;

wherein when the pair of jaws are in the fully opened condition the pair of jaws extend radially beyond the outer diameter of the outer tube; and when the pair of jaws are in the at least one approximated condition the pair of jaws have a transverse dimension equal to or less than the outer diameter of the outer tube.

14. The endoscopic surgical clip applier according to claim 13, wherein the endoscopic assembly includes a biasing member operatively coupled to the wedge plate, the biasing member configured for urging the wedge plate towards a position wherein the nose thereof is interposed between the pair of jaws.

15. The endoscopic surgical clip applier according to claim 13, wherein the release mechanism of the endoscopic assembly includes an inner shaft having a distal end portion operatively coupled to the wedge plate and a proximal end portion accessible for actuation of the release mechanism.

16. The endoscopic surgical clip applier according to claim 15, wherein the inner shaft is actuatable between:
   a first position wherein the nose of the wedge plate is interposed between the pair of jaws; and
   a second position wherein the nose of the wedge plate is withdrawn from between the pair of jaws,
   wherein actuation of the inner shaft is independent of actuation of a trigger.

17. The endoscopic surgical clip applier according to claim 15, wherein the distal end portion of the inner shaft includes an attachment block and a proximal end portion of the wedge plate includes an attachment slot configured to receive the attachment block of the inner shaft to operatively couple the wedge plate and the inner shaft.

18. The endoscopic surgical clip applier according to claim 13, wherein the endoscopic assembly includes:
   a channel defined in the outer tube;
   an at least one surgical clip disposed within the channel of the outer tube; and
   a clip pusher configured to individually, distally advance the at least one surgical clip towards the pair of jaws while the pair of jaws are in the fully opened condition.

19. An endoscopic surgical clip applier for application of surgical clips to body tissue, the surgical clip applier comprising:
   an endoscopic portion including:
      an outer tube having an outer diameter and defining a channel therein;
      at least one surgical clip disposed within the channel of the outer tube;
      a pair of jaws supported at a distal end of the outer tube, wherein the pair of jaws are movable between a fully opened condition and at least one approximated condition;
      a wedge plate slidably disposed within the endoscopic portion, the wedge plate defining a nose at a distal end thereof, wherein the wedge plate is movable between:
         a distal-most position wherein the nose is interposed between the pair of jaws to maintain the pair of jaws in the fully opened condition; and
         at least one proximal position wherein the nose of the wedge plate is at least partially withdrawn from between the pair of jaws to permit the pair of jaws to be placed in the at least one approximated condition;
      a clip pusher configured to individually, distally advance the at least one surgical clip towards the pair of jaws while the pair of jaws are in the fully opened condition; and
      a release mechanism connected to the wedge plate, the release mechanism slidably disposed within the outer tube and selectively directly actuatable from an exterior of the surgical clip applier, the release mechanism including a distal end coupled to the wedge plate and a proximal end projecting from within the surgical clip applier, wherein an actuation of the release mechanism withdraws the nose of the wedge plate at least partially from between the pair of jaws;
   wherein when the pair of jaws are in the fully opened condition the pair of jaws extend radially beyond the outer diameter of the outer tube; and when the pair of jaws are in the at least one approximated condition the pair of jaws have a transverse dimension equal to or less than the outer diameter of the outer tube.

20. The endoscopic surgical clip applier according to claim 19, wherein the release mechanism of the endoscopic assembly includes an inner shaft having a distal end portion operatively coupled to the wedge plate and a proximal end portion accessible for actuation of the release mechanism, wherein the inner shaft is actuatable between:
   a first position wherein the nose of the wedge plate is interposed between the pair of jaws; and
   a second position wherein the nose of the wedge plate is withdrawn from between the pair of jaws,
   wherein actuation of the inner shaft is independent of actuation of a trigger.

\* \* \* \* \*